(12) United States Patent
Smith

(10) Patent No.: US 6,200,782 B1
(45) Date of Patent: Mar. 13, 2001

(54) CONSTRUCTION OF NUCLEOPROTEIN BASED ASSEMBLIES COMPRISING ADDRESSABLE COMPONENTS FOR NANOSCALE ASSEMBLY AND NANOPROCESSORS

(75) Inventor: Steven S. Smith, Los Angeles, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 08/776,927

(22) PCT Filed: Jun. 7, 1995

(86) PCT No.: PCT/US95/07527

§ 371 Date: Apr. 11, 1997

§ 102(e) Date: Apr. 11, 1997

(87) PCT Pub. No.: WO96/05325

PCT Pub. Date: Feb. 22, 1996

Related U.S. Application Data

(63) Continuation-in-part of application No. PCT/US95/09085, filed on Aug. 12, 1994.

(51) Int. Cl.[7] .............................. C12P 19/34; C12Q 1/68
(52) U.S. Cl. ................................ 435/91.2; 435/6
(58) Field of Search ................... 435/6, 91.2, 4

(56) References Cited

U.S. PATENT DOCUMENTS 5,118,801   6/1992   Lizardi et al. ................. 536/27

FOREIGN PATENT DOCUMENTS

97/11972   *   3/1997   (WO) .

OTHER PUBLICATIONS

Prasad et al PNAS 92: 12160–12164, 1995.*

Hardy, T.A. et al., "Size of the Directing Moiety at Carbon 5 of Cytosine and the Activity of Human DNA(Cytosine–5)Methyltransferase", *Biochem. Biophys. Res. Commun.*, May. 29, 1987, vol. 145, No.1, pp. 146–152.

Dubey, A.K. et al., "Purification and characterization of the Mspl DNA methyltransferase cloned and overexpressed in *E. coli*"*Nucleic Acids Research*, 1992, vol. 7, pp. 1579–1585.

Chen, L. et al., "Direct Identification of the Active–Site Nucleophile in a DNA(Cytosine–5)–methyltransferase", *Biochemistry*, 1991, vol. 30, pp.11018–11025.

Seeman, "Branched DNA: A 3–D Structural Design System", *Clinical Chemistry*, vol. 39, No.4, pp. 722–726.

Osterman, D.G. et al., "5–Fluorocytosine in DNA is a Mechanism–Based Inhibitor of Hhal Methylase", *Biochemistry*, 1988, vol. 27, pp. 5204–5210.

Smith, S.S. et al., "Mechanism of human methyl–directed DNA methyltransferase and the fidelity of cytosine methylation", *Proc. Nat. Acad. Sci. USA*, May. 1992, vol. 89, pp. 4744–4748.

Friedman, S. et al., *Nucleic Acids Res.*, 1992, vol. 20, p. 3241–3248.

Baker, D.J. et al., "Transition State Analogs as Affinity Labels for Human DNA Methyltransferases", *Biochem. Biophys. Res. Commun.*, 1993, vol. 196, pp. 864–868.

Marasco, Jr., C.J. et al., *J. Org. Chem.*, 1992, vol. 57, pp.6363–6365.

McClellend, M. et al., *Gene*, 1988, vol. 74, pp. 294–304.

Klimasauskas, S. et al., *Cell*, 1994, vol. 76, pp. 357–369.

Kallenbach, N.R. et al., *Nature*, 1983, vol. 305, pp. 829–831.

Lauster, R. et al., *J. Mol. Biol.*, 1989) vol. 206, pp. 305–312.

* cited by examiner

Primary Examiner—Eggerton A. Campbell
(74) Attorney, Agent, or Firm—Rothwell, Figg, Ernst & Kurz

(57) ABSTRACT

A nucleoprotein based nanoprocessor is described. The nanoprocessor includes one or more chimeric fusion proteins linked to a DNA scaffold. Both components of the fusion protein are enzymes.

31 Claims, 10 Drawing Sheets

| | | |
|---|---|---|
| 8mer₂: | 5' | CGTT ⟩ |
| | 3' | GMTT |
| 16mer₂: | 5' | TCCGGGTT ⟩ |
| | 3' | AGGMCCTT |
| 24mer₂: | 5' | GATCCGGGCTTT ⟩ |
| | 3' | CTAGGMCCGATT |
| 32mer₂: | 5' | CAGATCCGGGCTACTT ⟩ |
| | 3' | GTCTAGGMCCGATGTT |
| 48mer₂: | 5' | CCACCAGATCCGGGCTACCTGGTT ⟩ |
| | 3' | GGTGGTCTAGGMCCGATGGACCTT |
| 96mer₂: | 5' | ACCAGGTCAGGTCCACCAGATCCGGGCTACCTGGGACTGGACCTAGTT ⟩ |
| | 3' | TGGTCCAGTCCAGGTGGTCTAGGMCCGATGGACCCTGACCTGGATCTT |

*IF ALL ENZYMES APPROACH FROM THE MAJOR GROOVE, HpaII WILL BE ON ONE SIDE OF THE HELIX WHILE HhaI AND HaeIII WILL BE ON THE OTHER IN THIS EXAMPLE.

H = HindIII
B = BamHI
Bg = BglII
N = NdeI

CONSTRUCTION OF NUCLEOPROTEIN BASED ASSEMBLIES COMPRISING ADDRESSABLE COMPONENTS FOR NANOSCALE ASSEMBLY AND NANOPROCESSORS

RELATED APPLICATIONS

This application is a 371 of PCT/US95/07527, filed Jun. 7, 1995, which is a continuation-in-part of PCT/US94/09085 filed Aug. 12, 1994.

BACKGROUND

Biological systems approach the limits of miniaturization. Both the proteins and nucleic acids found in biological systems are currently being manipulated using modern biotechnology. Recent progress in protein engineering clearly shows that the principles of the design and production of proteins of almost any desired functionality are now available. These principles have now been applied to the production of completely new proteins designed with detailed knowledge of protein structure and function (1).[1]

[1] See the bibliography list following the specification.

A logical next step in biotechnology is the fabrication of assemblies and devices on the nanometer scale. Since most devices take advantage of the proximity and precise 3D arrangement of individual components, one of the limitations in the fabrication of nanoscale devices has been the inherent lack of specificity in chemical methods for addressing components like bioengineered proteins to precise locations in a 2D array or 3D lattice.

The modular assembly of arrays is easily approached with DNA. Branching through the formation of Watson-Crick paired duplexes in the shape of a Y or an X is now well known (2–5), and Seeman and co-workers have pioneered the assembly of these modules into arrays and lattices with considerable success. Their experiments have demonstrated the feasibility of assembly of 2-D quadrilaterals and 3-D cubes on which more extended structures can be based.

More recently the synthesis of branching dendritimers of single stranded DNA has been reported (6). These components employ controlled introduction of bifunctional phosphoramidite which can cross-link chains in order to assembly precisely defined branched molecules.

While a 2-D or 3-D lattice of B-DNA having considerable complexity can now be constructed (7–8), only a limited number of applications can be envisioned for these structures unless addressable linking of useful components can be achieved. Seeman and co-workers have proposed devices based on the docking of conducting polymers or the attachment of enzymes through an antibody linkage (4,5). To date, antibodies directed against DNA have been difficult to produce and those that have been prepared have only a limited capacity to recognize DNA sequence. Thus, the selectivity of an antibody-based addressing system is questionable. Recognition of an organic hapten might provide more specificity. Here one would introduce a substitution at a prescribed site during synthesis into the DNA. Antibodies to the hapten could be used to decorate the matrix depending on the pattern laid down during synthesis. If the antibodies were engineered to be bifunctional, then they could be used as secondary attachment sites for a second antigen. The disadvantage here is that all hapten moieties are equivalent and thus selective addressing would not be possible unless a series of haptens and antibodies directed to them could be developed. Similar considerations hold for ligand binding systems like avidin-biotin. While a system of distinct haptens and antibodies is possible, developing a set of hapten-phosphoramidites and the series of bifunctional antibodies would be exceedingly time consuming. Moreover, the use of non-covalent linkages in order to achieve addressing would sacrifice stability.

The DNA(cytosine-5)methyltransferases may provide a key advance in addressable linking. The properties of DNA-(cytosine-5)methyltransferases that are useful in this context are: (1) the well-characterized DNA sequence specificities of the various bacterial enzymes (9), and (2) the formation of a dihydrocytosine intermediate during catalysis which results in the formation of a covalent complex between a group at the active site and 5-fluorocytosine (5-FdC) at the cytosine methylacceptor in the DNA recognition sequence of the methyltransferase (10–13).

In the biological catalysis carried out by the enzymes (FIG. 1), nucleophilic attack at C-6 of the cytosine ring in the DNA recognition site of the enzyme saturates the 5–6 double bond to produce a dihydrocytosine intermediate activated as a methylacceptor at C-5. The methyltransferase catalyzes methlytransfer to C-5 from S-adenosylmethionine to produce S-adenosylhomocysteine. β-elimination of the enzyme and the hydrogen at C-5 produces 5-methylcytosine and active enzyme. This process cannot be completed when 5FdC is attacked because both the C—C bond to the methyl group and C—F bond at C-5 are too strong to permit abstraction of either the methyl or the fluorine at C-5 as is required for β-elimination to proceed. The net result of enzymatic attack of 5FdC is the production of a stable covalent complex between the enzyme and DNA at specific DNA recognition sites containing 5FdC (16). See FIGS. 1 and 2A. A model of the enzyme covalently bound to an extended DNA molecule is depicted in FIG. 2B.

The recent elucidation of the three-dimensional structure of the HhaI methyltransferase covalently bound to 5FdC at its DNA recognition site shows that the covalent complex is further stabilized by enzyme-DNA contacts which give it its sequence recognition specificity (15).

SUMMARY OF THE INVENTION

This invention solves the problem of selective addressing by using the capacity of DNA(cytosine-5) methyltransferases to recognize specific DNA sequences and to form covalent suicide complexes with these sites when their target cytosines are replaced with 5-FdC. For example, HhaI recognizes the DNA tetramer GCGC while HaeIII recognizes the sequence GGCC. If 5-FdC (F) is placed at the target cytosines in each recognition sequence (GFGC for HhaI and GGFC for HaeIII) then the first sequence would be an address for HhaI and the other would be an address for HaeIII. Pursuant to this invention, by fusing functionally interesting proteins to any of a number of the cytosine methyltransferases which have been cloned, these functional proteins can be ordered in a preselected manner within a DNA array containing appropriate recognition sequences.

The invention also includes the discovery that FdC at a methyltransferase recognition sequence in DNA slows methyltransferase the reaction. The invention includes a non-denaturing gel system useful, inter alia, for the isolation of covalently linked complexes in native form and in high yield and overall yield for single site complexes to over 60% of input methyltransferase is observed.

The invention also includes the expression of methyltransferase genes such as the HhaI gene in bacteria. The expression of HhaI in *E. coli* strain RRI has been demonstrated. Preferable center-to-center spacing of methyltransfer genes on DNA has been determined utilizing, inter alia, mobility shift data.

The invention also includes the discovery that restriction enzymes for methyltransferase such as HhaI cleave at DNA sites already occupied by covalently bound methyltransferase, whereas non-cognate restriction enzymes do not cleave DNA sites within the footprint of the bound HhaI methyltransferase.

DETAILED DESCRIPTION OF THE INVENTION

Figure 6A:
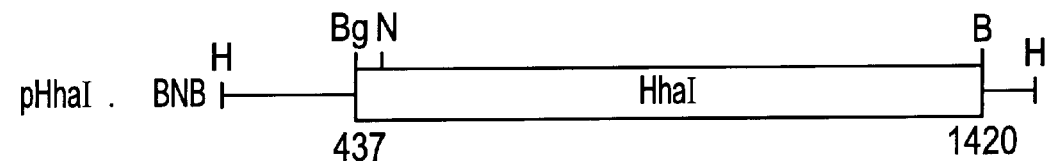
FIG. 6A is a schematic depiction of plasmids formed by polyermase chain reaction (PCR) modification of methyltransferase genes in preparation for assembly of the recombinant gene for the HhaI—HhaI homochimeric fusion protein.
Figure 6A:
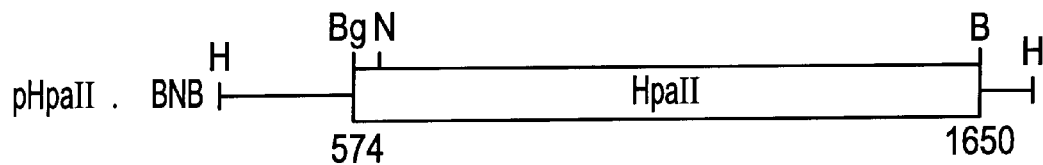

The range of useful structures and devices subsumed by the invention is quite large. As one example, an artificial synaptonemal complex could be constructed by linking four DNA duplexes in parallel and in register using bifunctional methyltransferases of the type described in FIG. 6A. The availability of large quantities of structures of this type with any desired juxtaposition of DNA sequences could open new molecular approaches to the biology of meiotic recombination and repair.

As a second example, controlled juxtaposition of two proteins in a scaffold could provide a tool for the purification and demonstration of interaction between proteins that interact with more than one target protein.

INTRODUCTION OF 5FdC INTO DNA

Three methods are available for the introduction of 5FdC into DNA. The first method was developed by applicant. It is a biosynthetic method that employs DNA polymeraseI to introduce 5FdC into a growing nucleotide chain using 5FdCTP as a precursor (12, 14).

The second method (17) involves the production of the 5-fluorocytosine phosphoramidite itself, followed by standard automated synthesis of DNA. This phosphoromidite is simpler to prepare than the 4-trimethylphenyl (TMP) derivative and requires no post-synthetic conversion step. The fluorine atom at C-5 deactivates the N-4 amino sufficiently to permit up to ten cycles of automated synthesis after the introduction of 5FdC. It is possible, however, that undesirable side reactions may occur in more extended molecules.

The third method developed by Verdine, et al. (11) is preferred. The phosphoramidite of the TMP derivative of 5-fluorouridine is incorporated into oligodeoxynucleotides and converted to 5PdC post-synthetically during the deprotection step. This method is also compatible with automated synthesis methods. Its implementation has been fully described by Verdine and co-workers (11) and is known to those skilled in the art.

METHYLTRANSFERASES USEFUL IN THE INVENTION

The principle of the addressing method of the invention stems from the availability of a series of methyltransferases with different sequence specificities which make the otherwise equivalent 5FdC residues distinguishable and therefore addressable because of DNA sequence context.

APPLICATION OF THE PRINCIPLES OF THE INVENTION

To apply the principles of the invention using a DNA cytosine methyltransferase, a preliminary characterization of the enzyme specificity is or has been carried out to determine its DNA recognition and its specificity for cytosine. A very large number of enzymes characterized in this way are currently known and have been listed in (9).

In order to proceed, a purification scheme is devised that will permit the purification of large quantities of the enzyme in a state that is both concentrated (at least 0.2 mg/ml) and substantially purified (if not homogeneous) so that the polypeptide chain corresponding to the enzyme itself is clearly visible in SDS acrylamide gels. This degree of purity has generally been achieved from biological sources (e.g., human tissue, bacterial cells, etc.) with a variety of liquid and high performance liquid chromatography steps that are known to those skilled in the art. Purification of enzymes whose protein and DNA sequence are known can be facilitated by enhanced expression achieved through genetic engineering methods also known to those skilled in the art. Purification methods developed for new enzymes from prokaryotic or from eukaryotic sources can be expected to follow the broad outlines of purification schemes already developed for enzymes from these sources. New procedures can be readily developed by those skilled in the art using available tools. While the ability to purify new methyltransferases may be required to practice this invention it is not viewed as part of the invention itself since the methods are available in general form for application to any new methyltransferase.

Nevertheless, this invention does include the discovery of a non-denaturing gel system for the isolation of covalently linked complexes in over 60% yield of the input methyltransferase.

More particularly, methyltransferase complexes may be efficiently purified by electrophoresis through a polyacrylamide gel using a gradient of polyacrylamide concentration becoming more concentrated in the direction of electrophoresis. Detergents such as SDS are omitted from such gels and electrophoresis is performed under conditions of pH and salt known to the art and effective to preserve the native state of the protein-DNA complex.

Once adequate amounts of purified protein are available, the enzyme should be characterized for use as an addressable component in nanoscale assemblies. Characterization may include (i) kinetic footprint determination, (ii) complex formation efficiency, and (iii) determination of minimum spacing.

KINETIC FOOTPRINT DETERMINATION

Each methyltransferase can be expected to have a unique footprint or area of direct contact with the DNA molecule. Since most of the known cytosine methyltransferases have recognition sequences between two and six nucleotides in length, one might expect that DNA molecules corresponding in length and recognition sequence to the recognition sequence itself would be long enough to permit efficient reaction with the methyltransferase. However, experience with the invention indicates that in order to achieve maximal coupling efficiencies, the molecules should be somewhat longer than the recognition sequence itself, probably because the region of contact between the enzyme and the DNA (generally known as its footprint) is a function of the size of the enzyme and the size of the recognition sequence.

Figure 1:
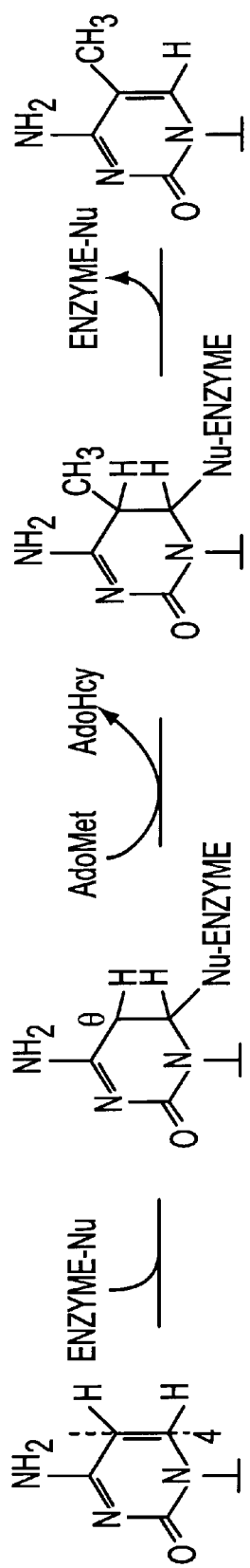
FIG. 1 depicts a methyltransferase mechanism.
Figure 2A:
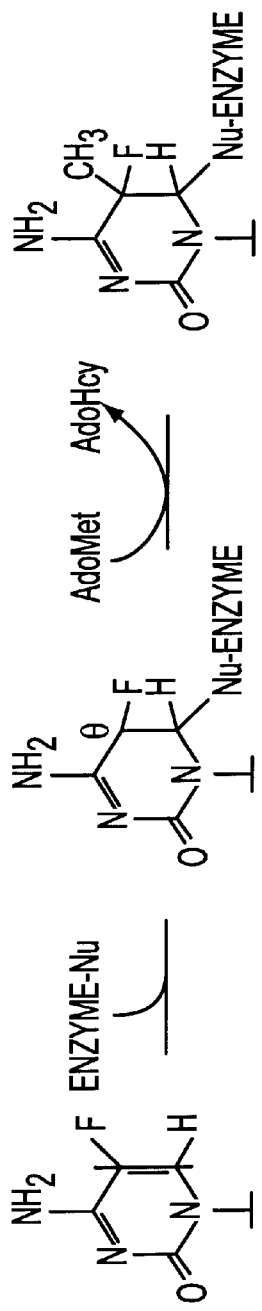
FIG. 2A depicts mechanistic steps in the formation of the complex between the enzyme and DNA at the DNA recognition site containing 5-FdC.
Figure 2B:
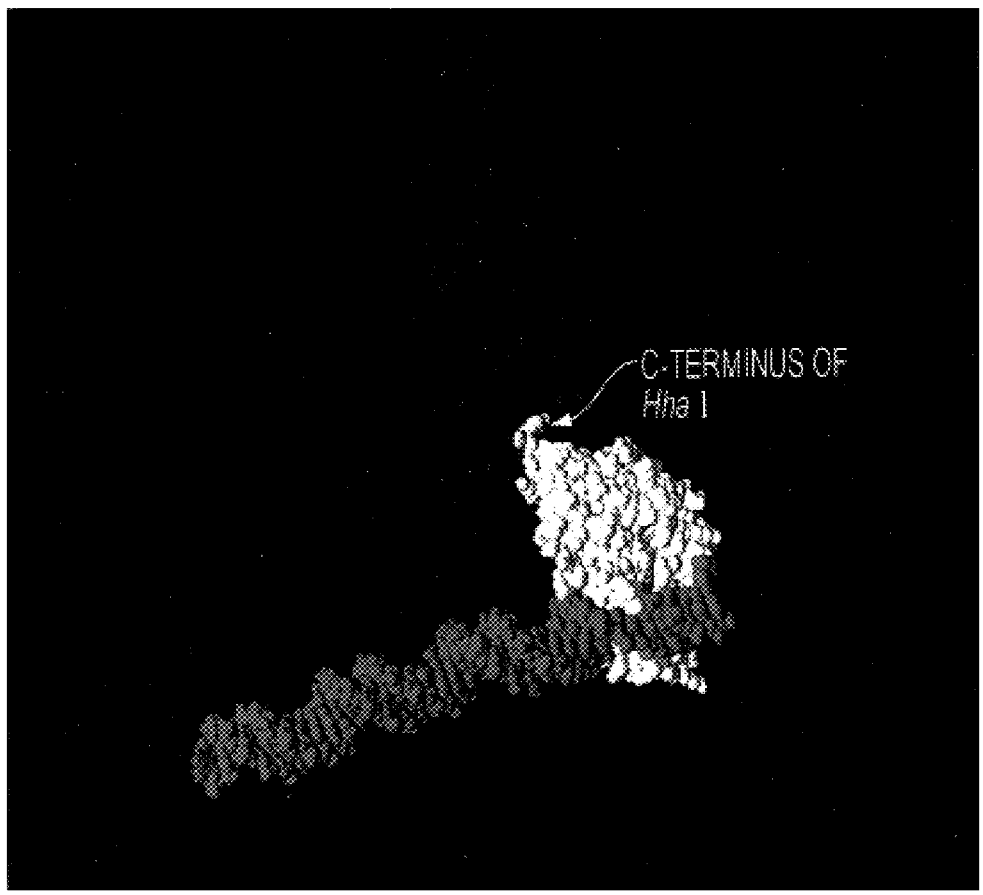
FIG. 2B depicts a model of the enzyme covalently bound to an extended DNA molecule.
Figures 3A, 3B:
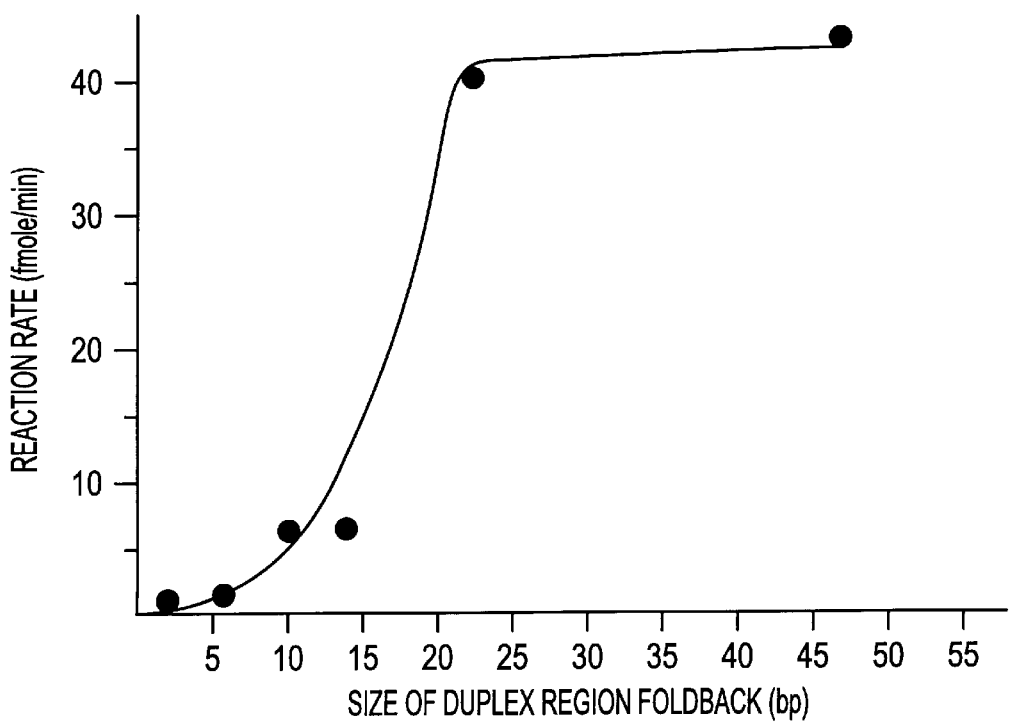
FIG. 3A depicts foldback molecules used as substrates for methyltransferase.
FIG. 3B is a curve which depicts the reaction rate as a function of the size of the test region of the molecules shown by FIG. 3A.

The following kinetic method should be used to determine the footprint and with it the length of DNA necessary for characterizing the optimal coupling efficiency as described below. Foldback molecules or linear duplexes composed of two complementary strands can be used as substrates in this method. In each molecule, a 5-methylcytosine residue is placed at one of the positions in the CG dinucleotide recognized by the human methyltransferase (FIG. 3A). The 5-methylcytosine (M) residue on one strand forces methylation of the CG dinucleotide on the complementary strand of the duplex (12). The homologous series of oligodeoxynucleotides is synthesized so as to place new base pairs on either side of the recognition site, thus symmetrically expanding the potential contact area in the DNA available for interaction with groups in the recognition site of the methyltransferase.

The results obtained with the human enzyme, which recognizes the CG dinucleotide (see FIG. 3B) indicate that the methyltransferase required at an absolute minimum 5 bp of duplex and is not further stimulated by sequences which provide more that 20 bp of duplex. For the purpose of this invention, this 20 bp number is interpreted as the physical extent of protein-DNA contacts along the DNA reflected by the kinetic data, i.e., the kinetic footprint of the methyltransferase.

Figure 3C:
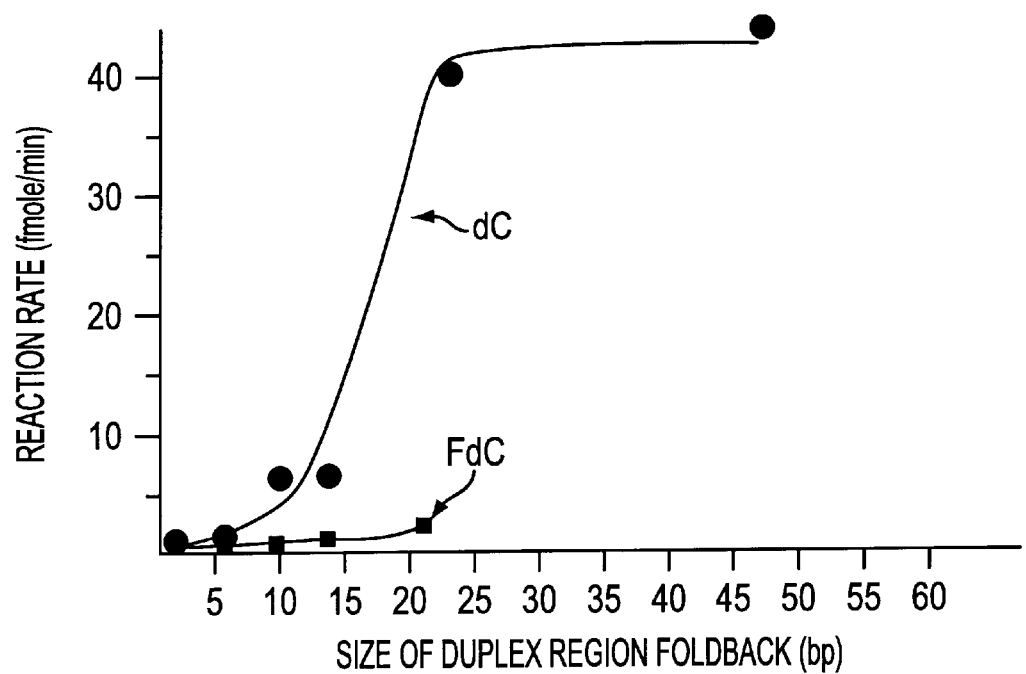
FIG. 3C depicts the effect of FdC substitution at the methyltransferase target site on reaction rate as a function of DNA length.

FIG. 3C depicts data indicating that foldback duplexes of various lengths having dC or FdC at the enzymatically targeted site of methylation were compared in otherwise identical reaction conditions given in Laayoun, A., *Nucleic Acids Res*, (24). The rate of methlytransfer, measured as the rate of incorporation of radiolabelled methyl-groups form [$^3$H-methyl]-S-Adenosyl-L-methionine into trichloroacetic acid insoluble DNA< was about forty fold lower for FdC containing DNAs regardless of length.

It is important to recognize that the kinetic footprint is the desired parameter here since it describes a reaction rate parameter. Physical footprints could be determined by other means but might or might not necessarily have the required bearing on the feasibility of a given assembly configuration.

COMPLEX FORMATION EFFICIENCY

For the initial characterization of the physical contacts required by a given enzyme the methylation rate can be used. However, the aim of the invention is to produce assemblies composed of enzyme-DNA complexes. Complex formation can be determined by following either of the components of the complex, protein or DNA. To follow DNA: A solution containing about 2 μm methyltransterase, 4–10 μm oligodeoxynucleotide containing an FdC at a site targeted for attack by the enzyme and having a length adequate to accommodate the kinetic footprint of the enzyme (determined as described above) is mixed with 50 to 100 μm S-adenosyl-L-methionine and allowed to react at 37° C. for eight hours. The reaction is sampled at intervals of two hours and the products are separated by molecular weight on SDS and the gels which are subsequently stained with ethidium bromide solution 1 μg/ml to quantify DNA. DNA can also be end-labelled with $^{32}$P or using $^{32}$P-ATP and T4 Polynucleotide kinase permitting labelled DNA to be detected by autoradiography (16). Complexes formed between the DNA and the protein are visualized by gel shift of the methyltransferase protein to higher molecular weight (see Example I for illustration).

To follow protein: A solution containing about 2 μm methyltransferase, 4–10 μm oligodeoxynucleotide containing an FdC at a site targeted for attack by the enzyme and having a length adequate to accommodate the kinetic footprint of the enzyme (determined as described above) is mixed with 50 to 100 μm S-adenosyl-L-methionine and allowed to react at 37° C. for eight hours. The reaction is sampled at intervals of two hours and the products are separated by molecular weight on SDS and the gels which are subsequently stained with Coomassie blue R250 to quantify protein. Complexes formed between the DNA and the protein are visualized by gel shift of the methyltransferase protein to higher molecular weight. The point at which the reaction is judged complete under these conditions is the point at which no further accumulation of methyltransferase protein at the mobility of the complex occurs. It should also correspond to the point at which the starting materials (methyltransferase protein, and DNA) are not further depleted.

Since enzymes having a cross-linking efficiency greater that 50% are preferred, the ratio of the material in the complex (visualized by observing protein or DNA) to that remaining at the methyltransferase molecular weight should be greater than 1. Such enzymes include HhaI and HhaIII. Others from the list of known enzymes which have not yet been tested (9) can be expected to possess useful cross-linking efficiencies.

DETERMINATION OF MINIMUM SPACING

To address multiple proteins to a single DNA strand, one must first determine how far apart recognition sequences must be spaced for efficient linking with methyltransferases. Since efficient linking requires accomplishing the linking rapidly and with high yield the minimum spacing should be determined kinetically. Pursuant to the invention, kinetic footprints are useful as a guide to minimize spacing between recognition sites in the construction of arrays. However, it is important to recognize that the HhaI methyltransferase is asymmetric (15) and based on sequence homology and physical studies, other methyltransferases can be expected to be asymmetric also. Thus the footprint of a given enzyme viewed as the area of direct contact with the DNA itself can be viewed as a minimum area of steric exclusion between two enzymes occupying the same DNA strand. Since domains outside the catalytic site of the protein might increase its bulk outside the region of contact with the DNA thus effectively preventing two enzymes from occupying sites with center to center distances that are 1 kinetic footprint apart, the following measurements are useful for efficient implementation of this invention.

Before proceeding with an untested enzyme, it is preferred to determine the closest placement that can be achieved with two copies of a single methyltransferase when DNA recognition sites are on the same DNA molecule. For closely juxtaposed sites, this evolves into two related questions. What is the effect of placing the target cytosines on the same side of the helix so that the enzyme molecules in the resulting product will be in a position on the same side of the DNA and what is the effect of placing the target cytosines on opposite sides of the helix so that the enzymes occupy space on opposite sides of the helix.

Since the period of the helix is 10 bp, these questions can be addressed by placing target cytosines at various distances from one another at center to center intervals for target cytosines of 5, 15, 25, 35, 45, and 55 bp in one homologous series of test oligodeoxynucleotides, and at center to center intervals for target cytosines of 10, 20, 30, 40, 50 and 60 bp in another homologous series. Using these homologous series of oligodeoxynucleotides a kinetic curve of the type shown for the initial kinetic footprint determination above can be used as an initial guide to minimum placement of the sites for the uncharacterized enzyme. When the sites are far enough apart to give efficient linking of two molecules of methyltransferase per chain a moderate transition to higher kinetic rate is expected. This is often obscured by the presence of two available sites for methyltransferase attack which results itself in the observation of an increased rate of the reaction.

Thus, the efficiency of the production of complexes containing two methyltransferases linked to the same DNA chain must be assessed using gel retardation as described above. In this application, complex formation can again be followed by using protein stain to detect methyltransferase in the complex, or by using radiolabelled or ethidium-bromide stained DNA to detect DNA in the complex.

An important aspect of this invention is the determination that a center-to-center spacing between methyltransferase recognition sites on DNA, e.g., linear DNA, is appropriate for nanoscale addressing.

When samples of reaction products from otherwise identical reactions, in which only the distance between recognition sites has been varied, are separated in adjacent lanes of a single SDS gel, a transition point indicating minimum distance between consecutive recognition sites should be observed. This will be most easily detected if the distance between the sites increases from left to right across the gel. In this case, a transition point should be observed at the first lane containing an oligodeoxynucleotide that permits the formation of significant amounts of a complex containing two copies of the methyltransferase (as judged by total molecular weight of the complex). To the left of this point complexes will be observed that contain only a single copy of the enzyme (as judged by total molecular weight of the complex) while to the right of this lane complexes will be observed that are of this molecular weight and also of a molecular weight corresponding to the presence of two copies of the enzyme on the same DNA molecule.

Complexes having two copies of the methyltransferase will generally be found to be formed more efficiently at spacings slightly beyond the initial transition point. Both oligodeoxynucleotide substrate series must be tested in order to determine these parameters for approach from the same side and from different sides of the helix. In general approach from different sides of the helix (tested with the series of cytosines of 5, 15, 25, 35, 45, and 55 bp apart) should be more efficient at closer spacings.

Once these tests have been performed on a given methyltransferase the parameters are used in design of assemblies as follows:

1. The kinetic footprint is taken as the minimum length of Watson-Crick-paired duplex DNA (generally between 10 and 30 bp) which can be used in the efficient assembly of a single enzyme-single oligodeoxynucleotide complex. This number is obtained by plotting the results of kinetic measurements using an oligodeoxynucleotide series containing a single recognition site.

2. The transition point in efficiently placing two copies of an enzyme along a single Watson-Crick-paired duplex is taken as the minimum spacing along a single duplex allowed for two recognition sites for the same enzyme. When placement on the same side of the helix is desired the number is derived from a plot of the data obtained with a homologous series of molecules having center to center spacings for the two sites of 10, 20, 30, 40, 50 and 60 bp. Data is preferably confirmed with gel electrophoretic analysis of the products. In general this number can be expected to be between 20% and 200% larger than the kinetic footprint.

3. The transition point in efficiently placing two copies of an enzyme along a single Watson-Crick-paired duplex is taken as the minimum spacing along a single duplex allowed for two recognition sites for the same enzyme. When placement on the same side of the helix is desired the number is derived form a plot of the data obtained with a homologous series of molecules having center to center spacings of the two sites of 5, 15, 25, 35, 45, and 55 bp. Data is preferably confirmed with gel electrophoretic analysis of the products. In general this number can be expected to be between 10% and 150% larger than the kinetic footprint.

METHOD FOR CONSTRUCTION OF DNA ARRAYS

Seeman, et al. have provided tools for the construction of DNA scaffolds in a variety of forms. Many of them involve modular construction from Y junctions and immobile holliday junctions (2, 3) which can be ligated together. In recent work, a duplex DNA molecule in the form of a cube (18), and a truncated octahedron (7) have been produced. These building blocks are thus available to anyone skilled in the art.

EXAMPLE I

Minimum Demonstration of 1-D Array Addressing to a Linear DNA

Figure 4A:
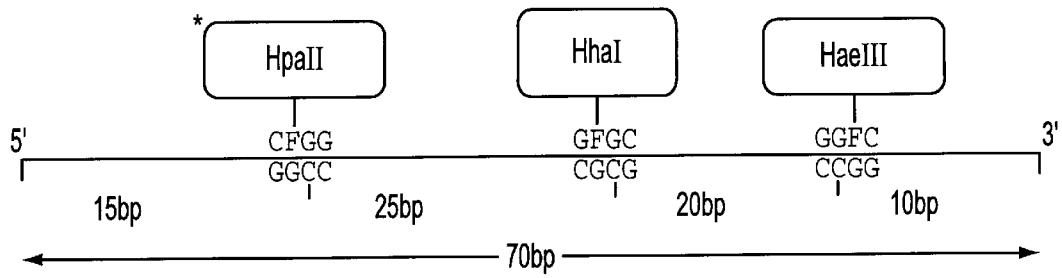
FIG. 4A is a schematic illustration of an oligodeoxynucleotide with three appropriately spaced recognition sites for three distinct methyltransferases.

Controlled addressing using heterologous methyltransferases having different kinetic footprints can be demonstrated by preparing an oligodeoxynucleotide with three appropriately spaced recognition sites for three distinct methyltransterases (FIG. 4A). Enzymes with small footprints and high yield coupling reactions as determined above are preferred.

The enzymes in the figure were chosen to depict the method. On the assumption that three of the four enzymes tested above have footprints of 16 bp or less, a 70 mer is constructed containing appropriate recognition sequence, e.g., CCGG for HpaII, GCGC for HhaI, and GGCC for HaeIII. Center to center distances between HpaII and HhaI recognition sites (25 bp for placement on different sides of the helix) and for HhaI and HaeIII (20 bp for placement on the same side of the helix) center to end distances for the 5' outside sequence (15 bp) and for the 3' end (10 bp) provide asymmetry useful in the analysis of restriction patterns required to confirm correct placement. Fluorocytosines are placed at the target cytosines in each of the recognition sequences on one strand. Cognate restriction enzymes are used to cleave the end-labelled 70 mer. Complete cleavage by a battery of three restriction enzymes will yield a 10 mer, a 15 mer, a 20 mer and a 25 mer. Cleavage at the 5' site (HpaII in this Example) will produce a 15 mer and a 55 mer: cleavage at the second site (HhaI in this example) will produce a 40 mer and a 30 mer cleavage at the third site (HaeIII in this Example) will produce a 60 mer and a 10 mer.

Stable complex formation can be demonstrated using the restriction enzymes to probe protection in the complexes. For example, if only the 5' site is coupled to its methyltransferase, then the gel retardation complex should have an appropriate mobility (see below) and only the restriction enzyme recognizing the 5' sequence should be unable to cut the oligomer. In this case, a gel retardation complex having an apparent mobility approximately equal to the sum of the molecular weights of the DNA and the methyltransferase as measured against protein standards. Here the mobility of the retardation complex carrying one DNA molecule and one copy of HpaII is expected to be about (358 amino acids/HpaII molecule×120 daltons/amino acid)+70 bp×330 daltons/bp)=42,960+23, 100=66,060 daltons.

Figure 4B:
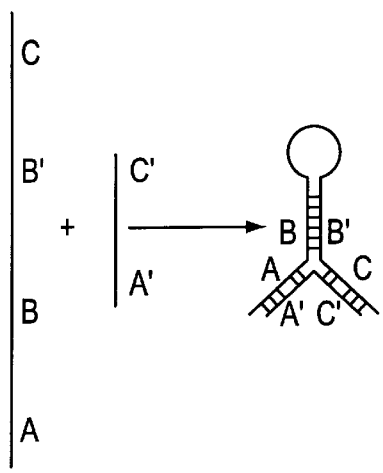
FIG. 4B is a schematic illustration of the invention as applied to an immobile Y junction of the type described by Seeman (5).

Addition of a copy of HhaI enzyme to the central site would produce a single enzyme complex of about 62,340 daltons. When two of the three sites are coupled, then the complex will be retarded further relative to the complex with a single coupled methyltransferase. This would raise the apparent molecular weight of the complex formed with HpaII by 39,240 daltons and produce a distinct band with mobility retarded to correspond to about 66,060+39,240= 105,300 daltons, moreover two of the three restriction enzymes HpaII and HhaI will now fail to cleave the complex. FIGS. 4A and 4B assume that the footprints of methyltransferases are similar to the footprints of their cognate restriction enzymes. The addition of the third enzyme HaeIII in this Example would raise the molecular weight of the complex to 144,900 daltons, allowing confirmation of the ready detection of the three enzyme complex. If the restriction enzymes require more space than the methyltransferases, larger oligodeoxynucleotides must be prepared to confirm that ordered linking has been achieved as indicated by gel retardation.

EXAMPLE II

Minimum Demonstration of 2-D Array Addressing to a Y-Junction

The same methods as described in Example I are applied to an immobile Y junction of the type described by Seeman (2). Simple immobile junctions can be constructed from two strands. The first strand must contain a region of internal complementarily (B and B') around the center of the molecule that extends half-way down its length, and produces a symmetrical stem loop structure, with two unpaired arms (A and C) equal in length to the stem. This molecule is hybridized with a shorter second strand of DNA complementary to the two free arms of the stem-loop strand (FIG. 4B). Each of the three double stranded regions in the structure can serve as a site of methyltransferase addressing. Thus the length of the arms in the structure will be chosen based on the outcome of the footprinting experiments and the 1-D addressing experiments. The three addresses (methyltransferase recognition sites) and the two ends available for end-labelling will permit analysis of the gel retardation products using the methods described above to demonstrate clearly controlled addressing.

EXAMPLE III

Construction of Fusion Genes, Proteins and Vectors

A key advance in nanoscale fabrication will be possible if a protein can be linked with a desired function to a methyltransferase, thereby rendering the function addressable. The major constraints on making fusion of proteins involve the capacity of proteins to fold properly in the fusion product. If for example the N-terminus or the C-terminus of either the methyltransferase or the protein of interest were placed in a region whose structural integrity was absolutely required for functionality, then a tandem fusion product would fold improperly, blocking the functionality of the protein. It would either fail to express methyltransferase activity or it would fail to express the linked activity of interest.

There is no general way to predict the outcome of such fusions and so it will be necessary to construct appropriately chosen fusion proteins and test their properties. Fortunately, three-dimensional structures are available for several interesting proteins and for one bacterial methyltransferase (15). Since there is a high degree of sequence homology between ethyltransferase (19), it is assumed that the general features of this structure will carry over to closely related enzymes like M·HaeIII and M·HpaIII and perhaps to M·SssI.

Figure 5A:
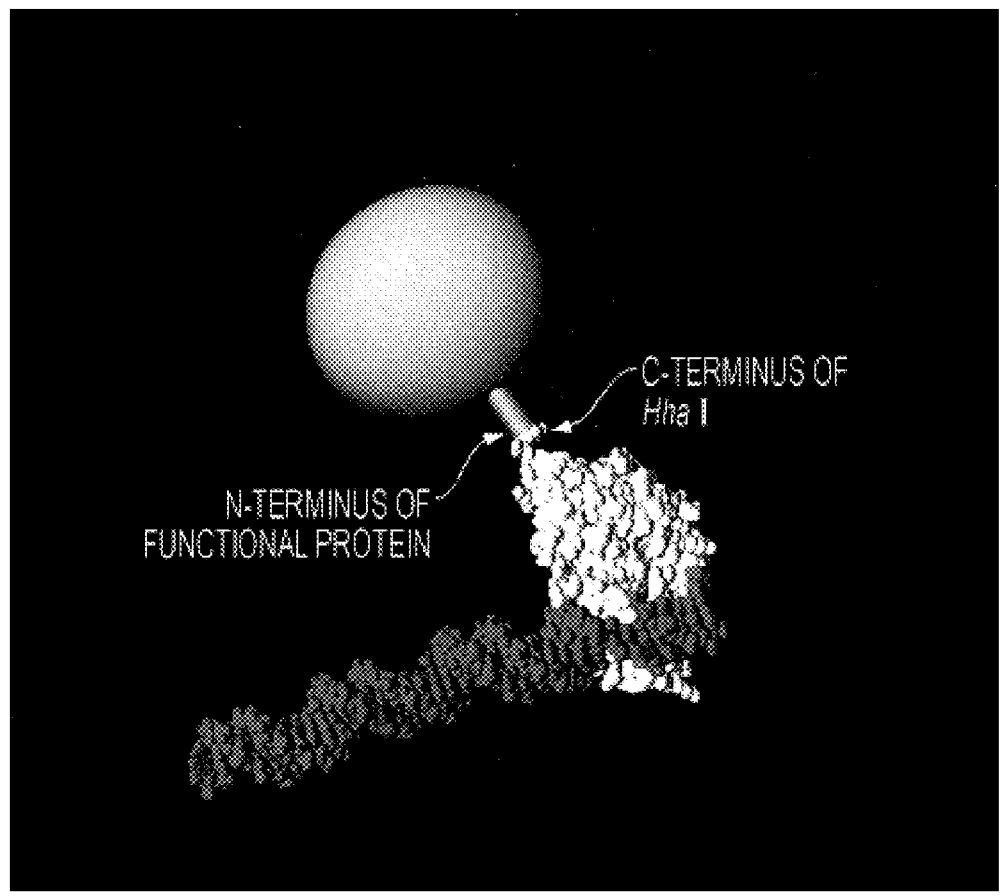
FIG. 5A depicts a model of the structure of M·HhaI in which M is a 5-methylcytosine residue.

The structure of M·HhaI suggests that the protein is exceptionally well suited for use as a linker in addressing fusion proteins. Among its nearly ideal features are the following (FIG. 5A): (1) its N-terminus and C-terminus are in close proximity to one another on the side of the protein opposite the DNA binding site, making it possible to express the fused functional protein at a right angle to the direction of the DNA chain; (2) neither the N-terminus nor the C-terminus are buried in the molecule suggesting that linkage at these sites will not disrupt methyltransferase activity; and (3) the C-terminus extends as a tail away from the tightly folded portion of the methyltransferase making it an ideal linker arm for connecting functional proteins (depicted as a sphere in FIG. 5A) in fusions.

Vector Constructions. As an example of appropriate cloning methods that may be employed, the construction of a fusion gene encoding a HhaI-HpaII heterochimeric protein is described. The same approach can be taken for making HhaI—HhaI homochimeric protein (FIG. 5B) or any other combination of functional domains described in this application.

To produce large quantities of chimeric protein, the pET-11a bacterial expression vector (20), which includes NdeI and BamHI cloning sites for inserting genes of interest, is used. As a first step for cloning into this vector, each methyltransferase gene (21, 22) is modified at its 5' end by adding BglII and NdeI sites immediately upstream of the initiating methionine, and at its 3' end by adding a BamHI site. Modification is performed by PCR and will result in the plasmids shown in FIG. 6A. Specifically, each methyltransferase gene to be used in the chimeric constructions will first be modified at its 5' end with BglII and NdeI sites, and at its 3' end with a BamHI site. These modifications will make the genes compatible with the pET-11a bacterial expression vector and allow construction of in-frame fusions between two methyltransferases in a head-to-tail fashion. Details of the HhaI cloning manipulations ar shown below in A. Similar steps will be performed for HpaII and the other methyltransferases, then cloning into the pET-11a vector will proceed as in (b).

(a) The HhaI gene is available on a plasmid containing the full-length, 1476 bp methyltransferase gene flanked by HindIII sites (21). The gene includes 5' and 3' untranslated sequences (solid line), and the complete HhaI open reading frame encoded from nt437-1417 (box). Cloning sites pertinent to this procedure are shown (H, HindIII; Bg, BglII; Bs, BsaAI; Hc, HincII; N, NdeI).

The desired restriction site insertions in the gene are accomplished as follows:

2. PCR to insert BamHI site at 3' end of coding region:

```
                                    HincII
5' primer:
5'-ACCC GTCAAC CAGCCAAGC-3' (SEQ ID NO. 3)
     1311        1329

HindIII   BamHI
3' primer:
5'-AACC AAGCTT GGATCC ATATGGTTTG-3' (SEQ ID NO. 4)
          1412   1408
```

PCR product digested with HincII+HindIII and inserted into HincII–HindIII (partial digest) sites of pHhaI. This removes the stop codon and inserts a BamHI site after the last codon of HhaI:

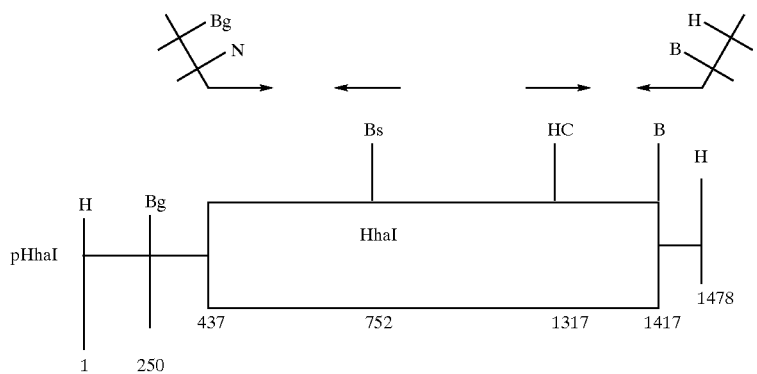

1. PCR to insert BglII-NdeI sites at 5' end of coding region (initiation codon in bold):

```
                                              BglII   NdeI
5' primer:
5'-ACGT AGATCT CATATG ATTGAAATAAAAG-3' (SEQ ID. NO. 1)
              437      452
                                              BasAI
3' primer:
5'-GACAA TACGT GCAATATC-3' (SEQ ID. NO. 2)
   760        743
```

PCR product digested with BglII + BasAI (N.E. Biolabs) and inserted into BglII BsaAI sites of pHhaI, giving:

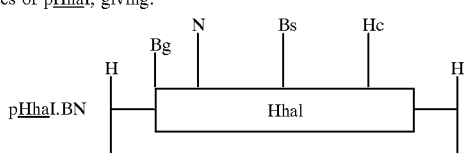

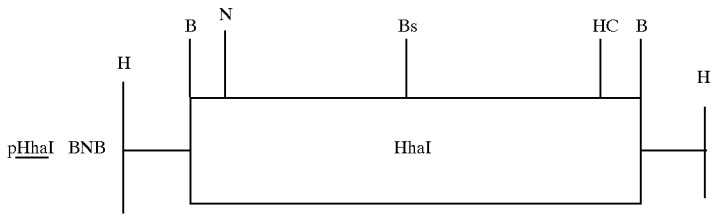

3. Similar steps are performed to create the HpaII vector (22):

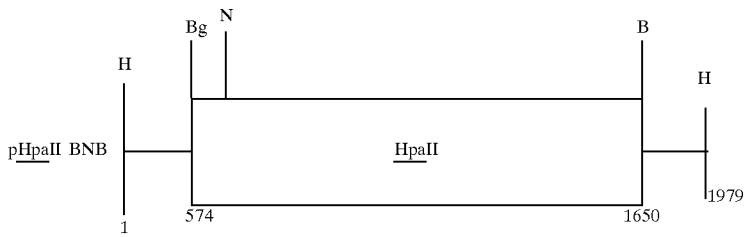

(b) The pET-11a expression vector contains unique NdeI and BamHI sites for insertion of foreign genes. The HhaI-HpaII fusion gene is constructed as follows:
1. NdeI-BamHI fragment from pHhaI.BNB is cloned into the NdeI-BamHI sites of pET-11a. The BamHI site remains unique.
BglII-BamHI fragment from pHpaII.BNB is cloned into the BamHI site downstream of the HhaI fragment in the expression vector.
The final plasmid construction contains the following:

SEQ ID NOS: 5–7.

Figure 6B:
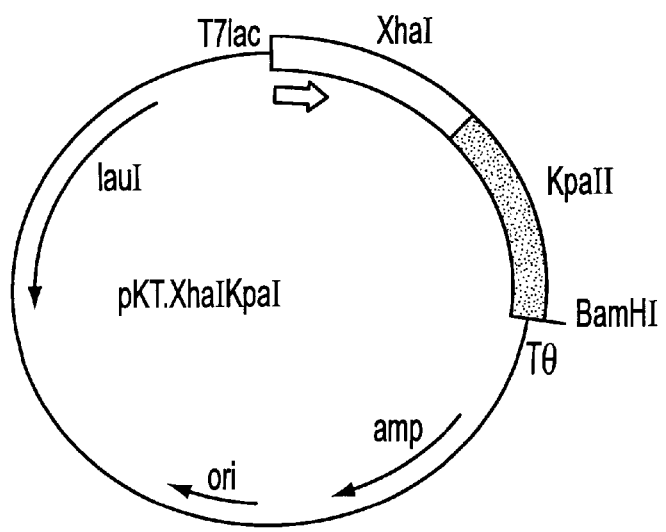
FIG. 6B is a map of a final expression vector with expression of the fusion gene driven by the T71ac promoter followed by a $T_0$ that transcription termination sequence recognized by $T_7$ polymerase.

To clone the modified HhaI gene into the bacterial expression vector in the upstream position, the NdeI-BamHI fragment form the pHhaI.BNB is inserted into the NdeI-BamHI site of pET-11a. The resulting plasmid is pET.HhaI. To clone the modified HpaII gene downstream of HhaI, the BglII-BamHI fragment form pHpaII.BNB is inserted into the BamHI site of pET-11.HhaI. An in-frame fusion gene encoding the entire HhaI protein, a 3 amino acid linker sequence, the entire HpaII domain, and a 4 amino acid extension at the C-terminus of the chimeric protein is produced. A map of the final expression vector is shown in FIG. 6B, with expression of the fusion gene driven by the T7lac promoter and followed by a T0 transcription termination sequence recognized by the T7 polymerase. Transcription proceeds in the direction of the arrows.

Bacterial Expression. To produce large quantities of chimeric proteins, vectors are transformed, for example, in known manner into a restrictionless derivative of BL21 bacteria carrying T7 polymerase under IPTG-inducible control. Expression is induced with IPTG and recombinant protein is purified by standard procedures, most of which are now employed in the laboratory for methyltransferase purification (12). The T7 lac promoter of pET-11a is under control of the lac repressor and the expression vector encodes the lacI repressor to ensure that expression of chimeric protein is inhibited in the absence of IPTG. However, if it is necessary to reduce potential toxicity of recombinant protein even further, bacteria will be co-transformed with a pLysS plasmid to inhibit leaky T7 polymerase synthesized in the absence of IPTG (20).

EXAMPLE IV

Figure 8:
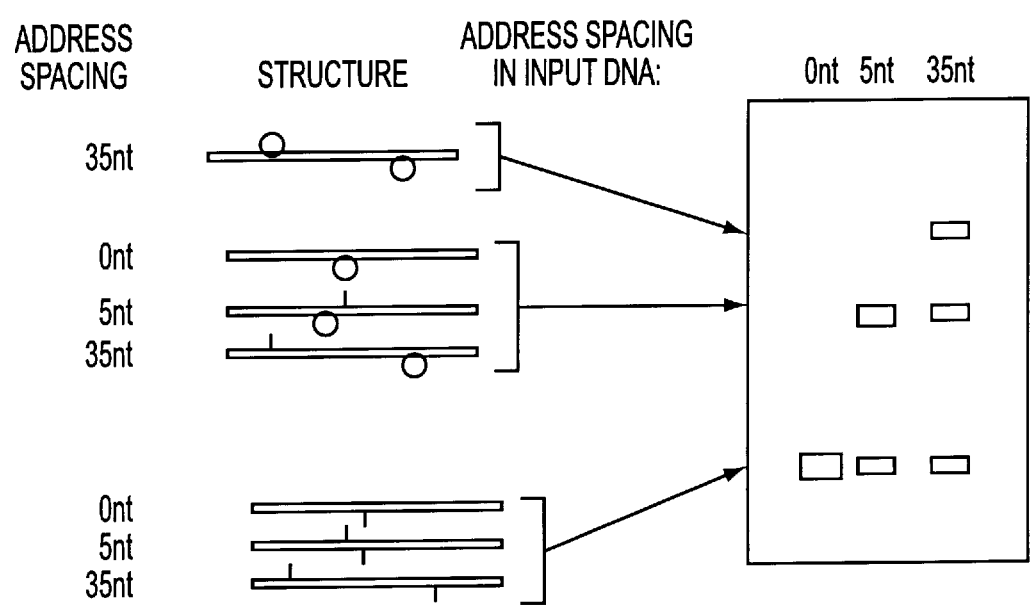
FIG. 8 is a schematic of gel electrophoretic demonstration of selective addressing.

This describes the experiments depicted by FIG. 8. Duplex DNA molecules with HhaI recognition sites (1) spaced 0 nt (nucleotides) 5 nt or 35 nt apart are allowed to react with the DNA methyltransferase. After the reaction the sequences were separated by electrophoresis through polyacrylamide gel (using a gradient of polyacrylamide concentrations becoming more concentrated in the direction of electrophoresis). Detergent (SDS) was omitted from these gels and electrophoresis was performed under conditions of pH and salt that preserve the native state of the protein-DNA complex. Those complexes with two addresses become cross linked to the methyltransferases at significant yield only when the recognition sites are placed 35 nt apart. Lanes: Ont: DNA with no address. 5 nt: DNA with two addresses 5 nt apart. 35 nt: DNA with two addresses 35 nt apart. Mobility shifts allow the demonstration of stoichiometry (i.e., molecules with two methyltransferases (indicated with large black spheres) move more slowly than molecules with one methyltransferase, which move more slowly than those with no methyltransferase). Stoichiometry corresponds to the occupation state of the addressed sites.

EXAMPLE V

Expression of the HhaI methyltransferase in E. coli RRI was demonstrated by isolating the pSP72.HhaI plasmid DNA from the transformed RRI host using standard miniprep techniques. The DNA was then shown to be refractory to cleavage by HhaI restriction endonuclease. Control pBR322 was then shown to be refractory to cleavage by HhaI restriction endonuclease. Control pBR322 grown in RRI but lacking the methyltransferase gene was cleaved by the HhaI restriction enzyme. This data indicates that the pSP72.HhaI DNA is protected from cleavage by HhaI restriction endonuclease because it is methylated by the HhaI methyltransferase expressed from the pSP72.HhaI plasmid. pBR322 transformed RRI does not express the methyltransferase gene and is therefore not protected from cleavage.

EXAMPLE VI

Linkage of Functionally Active Fusion Protein to a Scaffold

Figure 5B:
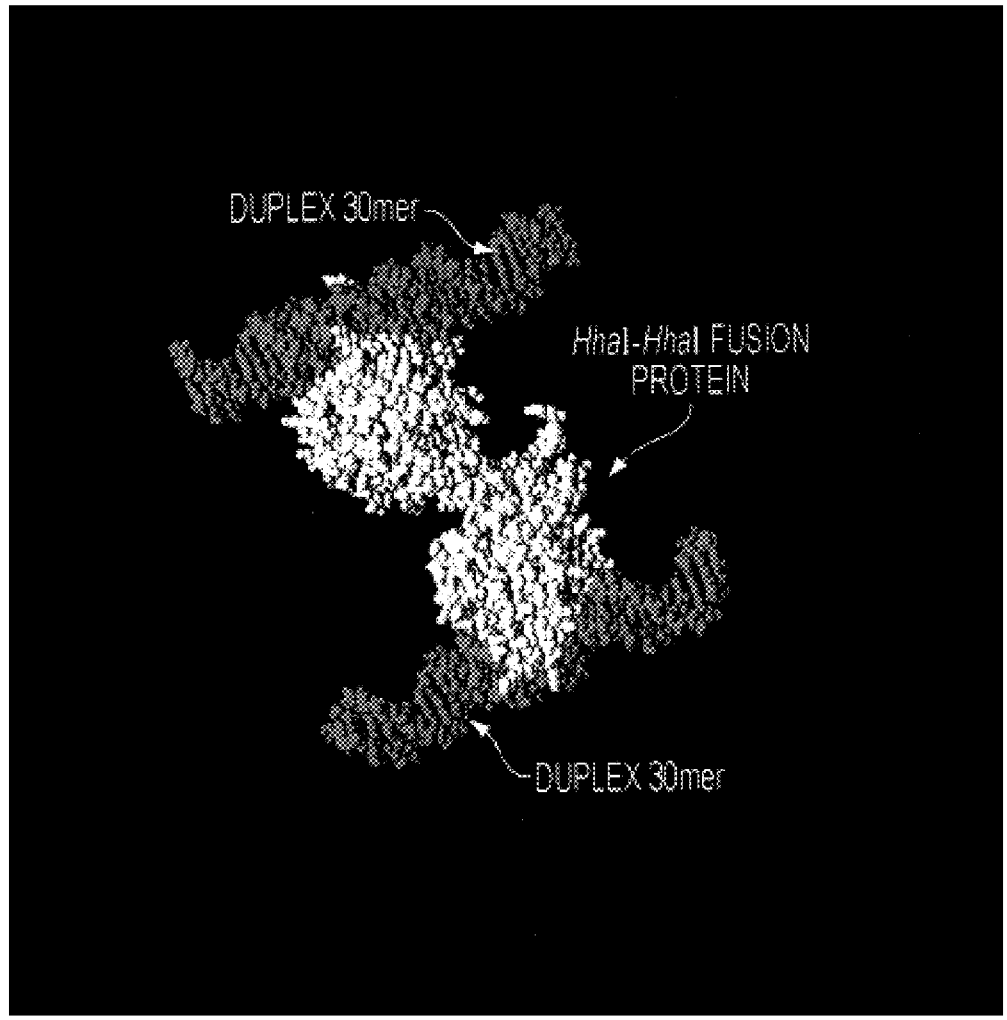
FIG. 5B depicts a model of the structure of HhaI—HhaI homochimeric protein.

As a minimum demonstration of the ability to link functionally an active fusion protein to a scaffold, the HhaI-HpaI bifunctional methyltransferase is used as a linker protein. Incubation of this protein with an end-labelled oligodeoxynucleotide carrying a recognition site for only one of the methyltransferases in the fusion will produce a gel retardation product with a unique mobility. Incubation of this complex with a second DNA (of different length) having a recognition site for the second methyltransferase will produce a second complex with a different mobility. Incubation of all three components (the bifunctional methyltransferase and two DNAs of different length) should produce a retardation complex with a third mobility if the bifunctional molecule can cross-link the two DNA molecules (FIG. 5B). Non-denaturing gels and SDS gels are expected to yield similar results.

The successful construction and testing of the fusion proteins described provides a basis for the development of a range of devices contemplated by the invention.

Catabolite-gene Activator Protein (CAP) is a positive transcription factor from *E. coli* which activates transcription from promoters sensitive to catabolite repression. It acts as a dimer in the presence of cyclic AMP (cAMP) by binding to its DNA recognition sequence and inducing it to bend. The crystal structure of the bent-DNA has been obtained (22) and visual inspection of the 3-D model of the structure available from the Brookhaven protein database suggests that pro9 at the N-terminus could be used in a head to tail linkage placing a bacterial methyltransferase in front of the CAP protein without disrupting the capacity of the protein to interact with itself in the dimer or with its DNA recognition site.

Figure 7:
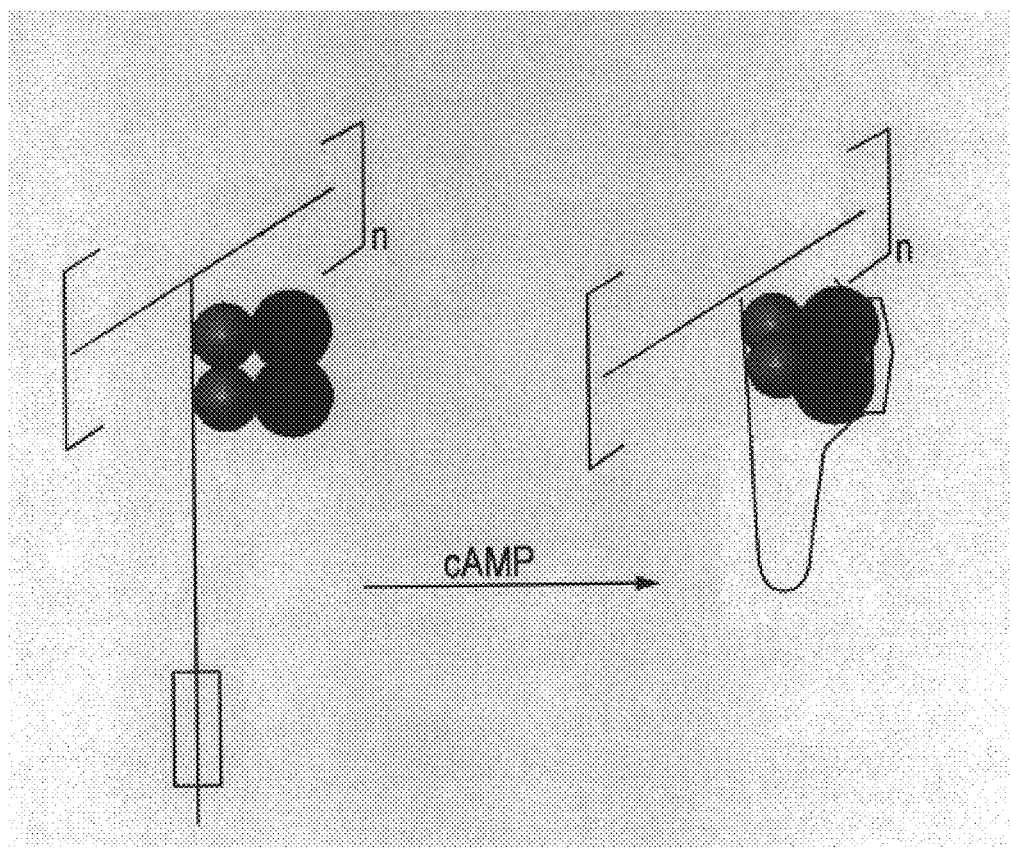
FIG. 7 depicts one schematic modular assembly contemplated by the invention.

If linking a methyltransferase to CAP monomers does not induce conformational changes in the complex that will preclude its interaction with DNA, then a methyltransferase-CAP fusion using the methods described above may be prepared. Two copies of the fusion adjacent to one another on an oligodeoxynucleotide (Y junction) containing a copy of the CAP recognition sequence at a distance far enough away from the point of methyltransferase attachment to permit formation in the presence of cAMP (FIG. 7) are linked.

Loop formation in this system should be dependent on the presence of cAMP. A change in the conformation of the biosensor will be detected as a gel mobility shift. An advantage of this system is the potential for modular assembly. Numerous elements of the type shown in FIG. 7 may be ligated together to form a long chain in which multiple conformational changes could be detected through physical techniques. Spectrophotometry could be used if a chromophore were linked to the DNA near the protein binding site.

BIBLIOGRAPHY

1. Hahn, K. W., et al. *Science* (1990) 248:1544.
2. Kallenbach, N. R., et al. *Nature* (1983) 305:829.
3. Dukett, D. R., et al., *Cell* (1988) 55:79.
4. Robinson, B. H., et al. *Prot. Eng.* (1987) 1:295 5–38.
5. Seeman, N. C., *Clinical Chem.* (1993) 39:722.
6. Hudson, R. G., et al., *J. Amer. Chem. Soc.* (1993) 115:2119.
7. Zhang, Y., at al., *J. Amer. Chem. Soc.* (1994) 116:1661.
8. Zhang, Y., et al., *J. Amer. Chem. Soc.* (1992) 144:2656.
9. McClellend, M., et al. *Gene* (1988) 74:291.
10. Osterman, D. E., et al. *Biochemistry* (1988) 27:5204.
11. Chen, L., et al. *Biochemistry* (1991) 30:11018.
12. Smith, S. S., et al., *Proc. Nat. Acad. Sci. USA* (1992) 89:4744.
13. Friedman, S., et al., *Nucleic Acids Res.* (1992) 20:3241.
14. Hardy, T. A., et al., *Biochem. Biophys. Res. Commun.* (1987) 145:146.
15. Klimasauskas, S., et al. *Cell* (1994) 76:357.
16. Baker, D. J., et al. *Biochem. Biophys. Res. Commun.* (1993) 196:864.
17. Marasco, Jr., C. J., et al. *J. Org. Chem.* (1992) 57:6363.
18. Chen, J., et al., *Nature* (1991) 350:631.
19. Lauster, R., et al., *J. Mol. Biol.* (1989) 206:305.
20. Studier, F. W., et al., *Methods Enzymol.* (1990) 185:60.
21. Caserta, M., et al., *J. Biol. Chem.* (1987) 262:4770.
22. Card, C. O., et al., *Nucl. Acids Res.* (1990) 18:1377.
23. Schultz, S. C., et al., *Science* (1991) 253:1001.
24. Laayoun, A. and Smith, S. S., *Nucleic Acids Res*, (1995) 23:1584–1589.

---

What is claimed is:

1. A complex comprising functionally ordered fusion proteins linked to a DNA sequence; wherein each of said fusion proteins comprises a first protein or peptide, wherein said first protein or peptide is a functional protein or peptide of interest, fused to a second peptide or protein that specifically recognizes and is covalently and stably linked to a recognition site at a desired position within the DNA sequence, thereby providing a covalent link between said first protein or peptide and said DNA sequence; and each of said recognition sites in said DNA sequence contains a trapping nucleotide within said recognition site which traps said second peptide or protein linked to said site and prevents it from releasing the DNA;

such that said functional peptides and proteins are linked to said DNA sequence in a desired functional order and in a desired orientation and at desired distances from one another.

2. A complex in accordance with claim 1, wherein each of said second peptides or proteins is a DNA methyltransferase and each of said recognition sites in said DNA sequence comprises a DNA methyltransferase recognition site.

3. A complex in accordance with claim 2, wherein said trapping nucleotide in each of said recognition sites has replaced a cytosine and said DNA methyltransferases are DNA (cytosine-5)methyltransferases.

4. A complex in accordance with claim 3, wherein said trapping nucleotide is a 5FdC.

5. A complex in accordance with claim 1, wherein said DNA sequence comprises at least two different recognition sites.

6. A complex in accordance with claim 2, wherein said DNA sequence comprises at least two different methyltransferase recognition sites.

7. A complex in accordance with claim 1, wherein each of said recognition sites in said DNA sequence are recognized by a preselected peptide or protein.

8. A complex in accordance with claim 2, wherein each of said methyltransferase recognition sites is recognized by a preselected methyltransferase.

9. A complex in accordance with claim 1, wherein said DNA sequence is linear.

10. A complex in accordance with claim 1, wherein said DNA sequence comprises an immobile X junction or an immobile Y junction.

11. A complex comprising functionally ordered fusion proteins linked to a DNA sequence; wherein each of said fusion proteins comprises a DNA(cytosine-5)methyltransferase fused to a functional peptide or protein, each of said methyltransferases specifically recognizes and is covalently linked to a DNA methyltransferase recognition site at a desired position within the DNA sequence, and each of said recognition sites contains a 5FdC in place of a methyltransferase target cytosine;

such that said functional peptides and proteins are linked to said DNA sequence in a desired functional order and at desired distances from one another.

12. A complex in accordance with claim 11, wherein said DNA sequence comprises at least two different methyltransferase recognition sites.

13. A complex in accordance with claim 11, wherein each of said methyl transferase recognition sites is recognized by a preselected methyltransferase.

14. A complex in accordance with claim 11, wherein said DNA sequence is linear.

15. A complex in accordance with claim 11, wherein said DNA sequence comprises an immobile X junction or an immobile Y junction.

16. A complex in accordance with claim 11, wherein said sequence is the sequence depicted in FIG. 4A.

17. A method of preparing a complex in accordance with claim 1, which comprises:

a) constructing a series of fusion proteins, each of said fusion proteins comprising a first functional protein or peptide of interest fused to a second peptide or protein which specifically recognizes and can covalently and stably link to a recognition site in a DNA sequence;

b) constructing a DNA sequence which comprises a specific recognition site for each of said second peptides or proteins at selected sites within said sequence, wherein said sites are selected such that they are in a desired order and at desired distances from one another, and wherein each of said recognition sites contains a trapping nucleotide which traps said second peptide or protein when said second peptide or protein links to said site and prevents it from releasing from the DNA; and c) reacting said DNA sequence with each of said fusion proteins under conditions whereby the second peptide or protein of each of said fusion proteins specifically recognizes and is covalently and stably linked to its recognition site within said DNA sequence; said trapping nucleotide preventing said second peptide or protein from releasing from the DNA.

18. A method in accordance with claim 17, wherein each of said second peptides or proteins is a DNA methyltransferase and each of said DNA recognition sites is said DNA sequence comprises a DNA methyltransferase recognition site.

19. A method in accordance with claim 18, wherein said trapping nucleotide in each of said recognition sites has replaced a cytosine and said DNA methyltransferases are DNA (cytosine-5)methyltransferases.

20. A method in accordance with claim 19, wherein said trapping nucleotide is a 5FdC.

21. A method in accordance with claim 17, wherein said DNA sequence comprises at least two different recognition sites.

22. A method in accordance with claim 18, wherein said DNA sequence comprises at least two different methyltransferase recognition sites.

23. A method in accordance with claim 17, wherein each of said recognition sites in said DNA sequence are recognized by a preselected peptide or protein.

24. A method in accordance with claim 18, wherein each of said methyl transferase recognition sites is recognized by a preselected methyltransferase.

25. A method in accordance with claim 17, wherein said DNA sequence is linear.

26. A method in accordance with claim 17, wherein said DNA sequence comprises an immobile X junction or an immobile Y junction.

27. A method of preparing a complex in accordance with claim 11, which comprises:

a) constructing a series of fusion proteins, each of said fusion proteins comprising a functional protein or peptide of interest fused to a specific DNA (cytosine-5) methyltransferase:

b) constructing a DNA sequence which comprises a specific recognition site for each of said methyltransferases at selected sites within said sequence, wherein said sites are selected such that they are in a desired order and a desired orientation and at desired distances from one another, and wherein each of said recognition sites contains a 5FdC in place of a methyltransferase target cytosine; and c) reacting said DNA sequence with each of said fusion proteins under conditions whereby the methyltransferase of each of said fusion proteins specifically recognizes and is covalently and stably linked to its recognition site within said DNA sequence.

28. A method in accordance with claim 27, wherein said DNA sequence comprises at least two different methyltransferase recognition sites.

29. A method in accordance with claim 27, wherein each of said methyltransferase recognition sites is recognized by a preselected methyltransferase.

30. A method in accordance with claim 27, wherein said DNA sequence is linear.

31. A method in accordance with claim 27, wherein said DNA sequence comprises an immobile X junction or an immobile Y junction.

* * * * *

SEQUENCE LISTING

<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 1

-continued

```
acgtagatct catatgattg aaataaaag                              29

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
gacaatacgt gcaatatc                                          18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
acccgtcaac cagccaagc                                         19

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
aaccaagctt ggatccatat ggtttg                                 26

<210> SEQ ID NO 5
<211> LENGTH: 7
<212> TYPE: DNA
<213> ORGANISM: Artificial Sequence
<220> FEATURE:
<223> OTHER INFORMATION: Description of Artificial Sequence: HhaI
      Plasmid Construct

<400> SEQUENCE: 5 attgatt                                                      7

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: HhaI
      Plasmid Construct

<400> SEQUENCE: 6
ccatatggat ctcatatgaa a                                      21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: HhaI
      Plasmid Construct

<400> SEQUENCE: 7
ccatatggat ccggctgcta a                                      21
```